United States Patent [19]

Greenawalt

[11] Patent Number: 5,443,079
[45] Date of Patent: Aug. 22, 1995

[54] ADJUSTABLE CHIROPRACTIC DIAGNOSTIC APPARATUS

[76] Inventor: Kent S. Greenawalt, 5056 Hunting Hills Sq., Roanoke, Va. 20414

[21] Appl. No.: 139,131

[22] Filed: Oct. 21, 1993

[51] Int. Cl.⁶ ............................................. A61B 5/103
[52] U.S. Cl. ................................................... 128/781
[58] Field of Search ................. 128/774, 782, 781; 33/511, 512

[56] References Cited

U.S. PATENT DOCUMENTS

| | | | |
|---|---|---|---|
| 4,036,213 | 7/1977 | Gregory | 128/781 |
| 4,135,498 | 1/1979 | McGee | 128/774 |
| 5,094,249 | 3/1992 | Marras et al. | 128/781 |
| 5,099,859 | 3/1992 | Bell | 128/781 |
| 5,147,372 | 9/1992 | Nymark et al. | 606/130 |
| 5,176,689 | 1/1993 | Hardy et al. | 606/130 |

Primary Examiner—Max Hindenburg
Attorney, Agent, or Firm—Henderson & Sturm

[57] ABSTRACT

An adjustable chiropractic diagnostic apparatus 910) for measuring the postural deficiencies of a patient (100) wherein, the apparatus (10) comprises a posterior (30) and a lateral (31) framework member each having a single vertical alignment cord (60)(60′) and a plurality of horizontal alignment cords (61)(61′)(62)(62′) which are connected together by body marker members (65) that are translatable to specific locations on the patient's body once the vertical (60) and lateral (61)(62) alignment cords have been aligned with other portions of the users body to produce a recordable record of the patient's postural deficiencies.

11 Claims, 2 Drawing Sheets

ADJUSTABLE CHIROPRACTIC DIAGNOSTIC APPARATUS

TECHNICAL FIELD

This invention relates to the field of diagnostic apparatus in general, and in particular, diagnostic apparatus in the chiropractic area which employs an adjustable grid system to record and evaluate a patient's postural misalignments.

BACKGROUND ART

As can be seen by reference to the following U.S. Pat. Nos. 5,147,372; 5,176,689; 5,094,249; and 5,099,859; the prior art is replete with myriad and diverse non-invasive diagnostic testing apparatus.

While all of the aforementioned prior art constructions are more than adequate for the basic purpose and function for which they have been specifically designed, these patented diagnostic apparatus, while containing some of the same general structural features and concept do not offer the degree of simplicity of use, as well as the flexibility and fine tuning of the alignment elements that are possible with the diagnostic structure that forms the basis of the present invention.

As in most diagnostic situations, the most commonly employed apparatus are those whose operation is relatively simple and straightforward as well as being highly accurate with regard to the measurements being taken and recorded.

Particularly with regard to chiropractic practice, many conditions and ailments may be traced to a postural condition which places under stress on vital nerves and tissues. As a consequence, the detection of these postural misalignments is imperative before any method of correction may be proscribed, and the state of the art among the chiropractic diagnostic apparatus currently available leaves much to be desired.

DISCLOSURE OF THE INVENTION

Briefly stated, the adjustable chiropractic diagnostic apparatus that forms the basis of the present invention comprises in general: a platform unit; a dual plane grid unit; and a plurality of moveable registration units which cooperate with one another to provide an accurate measurement of postural misalignments along an X, Y axes in both the posterior and lateral orientations of the patent.

As will be explained in greater detail further on in the specification, the registration units include both platform mounted and frame mounted registration members which include track mounted markers, and supports for a plurality of horizontally and vertically oriented elongated flexible strand elements which are operatively associated with one another by a plurality of body marking discs.

In the preferred embodiment of the invention, the patient initially is positioned relative to one or more of the registration units; whereupon, certain track mounted markers and supports are positioned in alignment with specified anatomical reference points on the patient's anatomy.

At this juncture, the horizontal strand elements are arrayed along other anatomical reference points, and then the body marking discs are then translated along the generally horizontal strand elements into registration with other anatomical reference points to angularly displace adjacent segments of the vertically oriented strand elements to produce an accurate and measurable representation of the patient's postural deficits and misalign.

BRIEF DESCRIPTION OF THE DRAWINGS

These and other attributes of the invention will become more clear upon a thorough study of the following description of the best mode for carrying out the invention, particularly when reviewed in conjunction with the drawings, wherein.

BEST MODE FOR CARRYING OUT THE INVENTION

Figure 1:
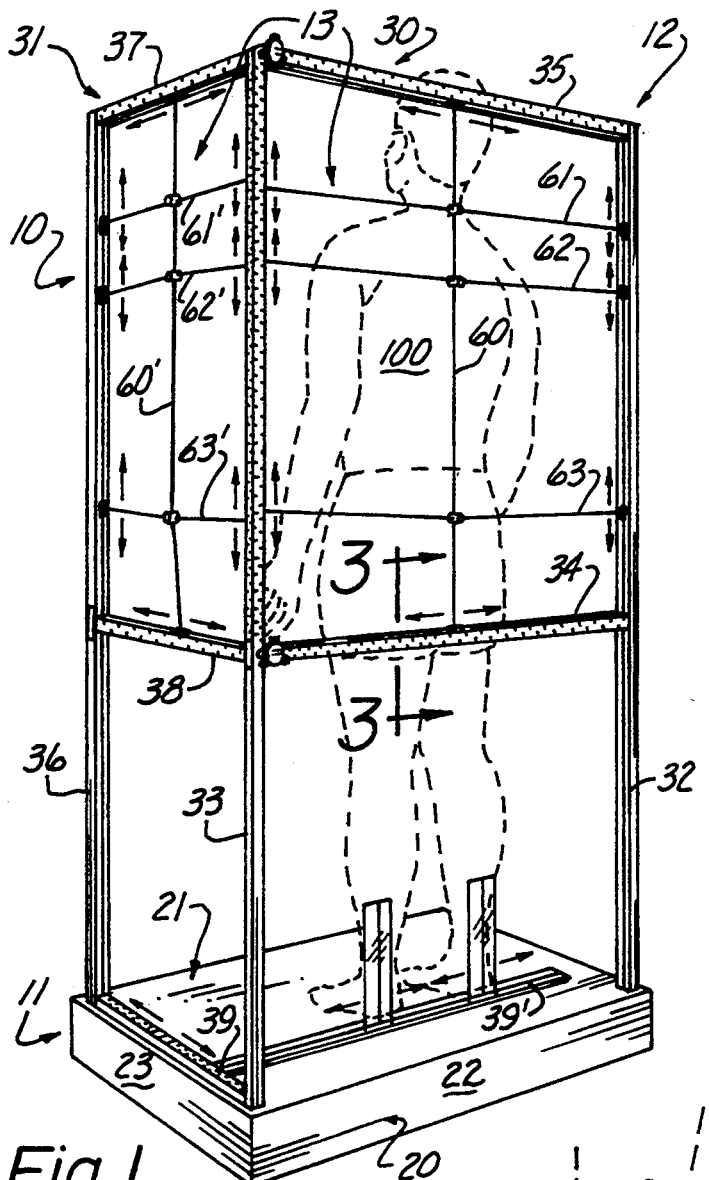
FIG. 1 a perspective view of the adjustable chiropractic diagnostic apparatus that forms the basis of this invention in use.

As can be seen by reference to the drawings, and in particular to FIG. 1, the adjustable chiropractic diagnostic apparatus that forms the basis of the present invention is designated generally by the reference numeral (10). The apparatus (10) comprises in general a platform unit (11); a dual plane grid unit (12); and a plurality of moveable registration units (13). These units will now be described in seriatim fashion.

As shown in FIG. 1, the platform unit (11) comprises an enlarged generally rectangular platform member (20) having a raised platform surface (21) which is dimensioned to receive and support a patient at a slightly elevated height.

Still referring to FIG. 1, it can be seen that the dual plane grid unit (12) comprises a pair of generally rectangular and perpendicularly aligned framework member (30)(31) which include a posterior framework member (30) and a lateral framework member (31) arrayed along adjacent sides of the platform surface, wherein, the adjacent edges of the posterior (30) and lateral (31) framework members are disposed perpendicular to one another.

As shown in FIG. 1, the grid unit (12) basically comprises a three-legged generally 2-shaped framework connected together by a plurality of cross-piece elements. The posterior framework member (30) comprises a pair of vertical support legs (32) and (33) disposed at opposite ends of one side (22) of the platform member (20), wherein, the vertical support legs (32) and (33) are provided with an upper (34) and an intermediate (35) cross-piece element.

In addition, the lateral framework member (31) also comprises a pair of vertical support legs (33) and (36) are provided with an upper (37), an intermediate (38), and a lower (39) cross-piece element, wherein all of the cross-piece elements share structural features in common, both with one another, and with the upper portions of the three vertical support legs (32)(33) and (36) as will be explained in greater detail further on in the specification.

Figure 7:
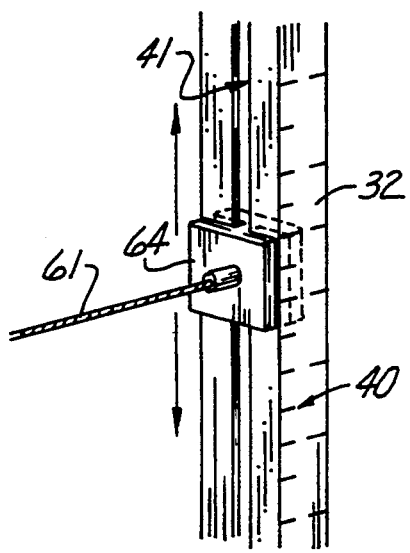
FIG. 7 an isolated perspective view of one of the tack mounted supports for one of the strand elements.

As can best be seen by reference to FIGS. 2, 3 and 7, all of the cross-piece elements (34) (35) (37)(38)(39) as well as the upper portions of the three vertical support legs (32) (33) and (36) are provided with measuring indica (40) and at least one slotted channel (41) dimensioned to receive the plurality of moveable registration units (13) which will be described presently.

Figure 2:
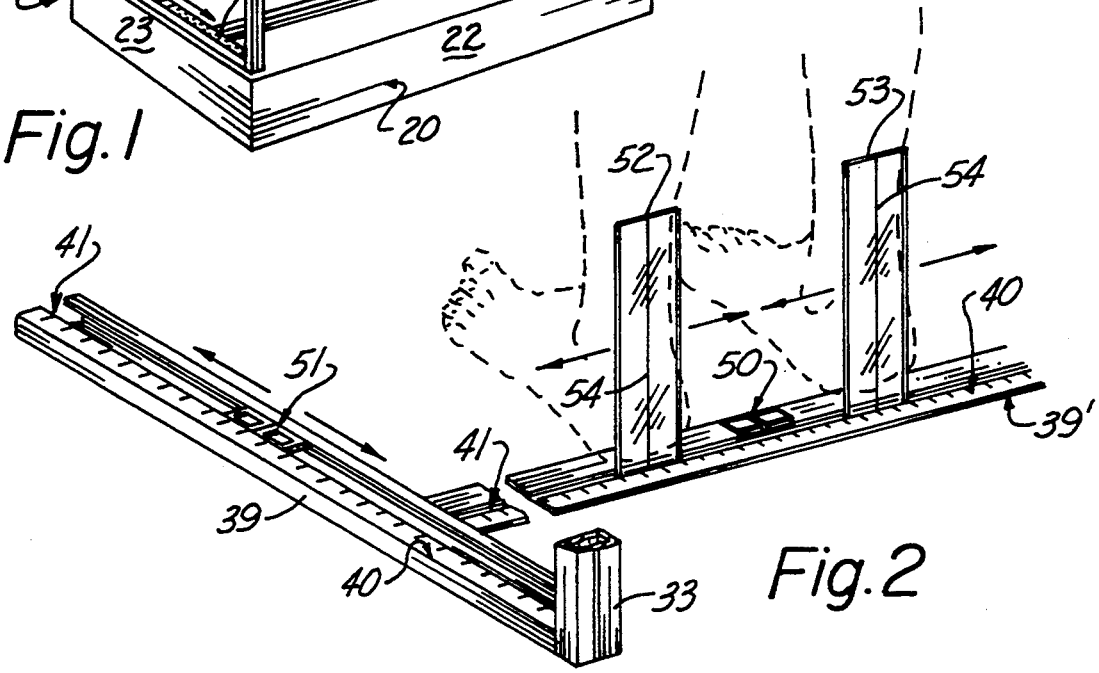
FIG. 2 an isolated perspective view of the platforms mounted moveable registration units.

In addition, as shown in FIGS. 1 and 2, the lower cross-piece element (39) of the lateral framework member (31) is further provided with a perpendicularly aligned extension are (39) which is disposed on the platform surface (21) proximate to, but spaced from the vertical support leg (33) which is shared by both the lateral (31) and the posterior (30) framework members, wherein, the extension arm (39) is also provided with a slotted channel (41) and indicia (40) similar to the aforementioned cross-piece elements.

Still referring to FIG. 2, it can be seen that the plurality of registration units (13) comprise in part a low profile midline marker (50) and low profile lateral foot marker (51); as well as a pair of vertically elongated transparent achilles tendon guides (52)(53); wherein, both the markers (50)(51) and the tendon guides (52)(53) are slideably disposed in the slotted channels (41) of the lower cross-piece element (39) and extension (39) respectively. As can also be seen by reference to FIG. 2, each of the transparent tendon guides (52)(53) is further provided with centerline indicia (54) to assist the user in aligning the tendon guides (52)(53) with the midline of the patient's right and left calcaneus as will be explained in greater detail further on in the specification.

Turning now to FIGS. 3, 4, 6 and 7, it can be seen that the posterior (30) and lateral (31) framework members are provided with vertical alignment cords (60)(60') as well as upper (61)(61') intermediate (62)(62') and lower (63)(63') horizontal alignment cords, wherein, all of the alignment cords are adjustably supported relative to the framework members (30((31) by cord anchor plates (64) which are slideably disposed in the slotted channels (41) formed in the framework member (30)(31).

Figure 3:
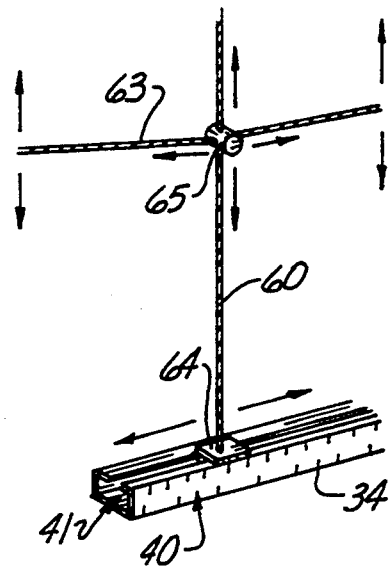
FIG. 3 an isolated perspective view of some of the moveable registration units employed on the grid unit.
Figure 5:
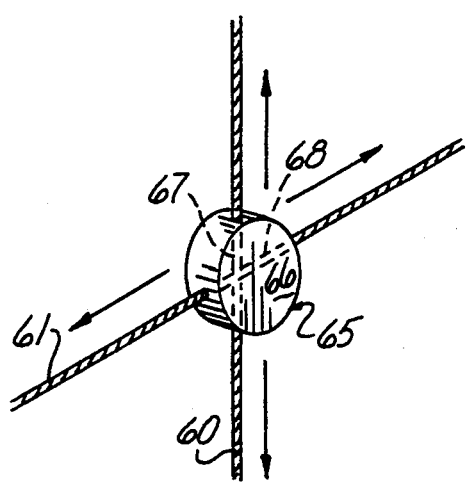
FIG. 5 an isolated perspective view of the cooperation of one of the body marking discs with a horizontal and a vertical strand element.

In addition, as shown in FIGS. 3 and 5, the registration units (13) further comprise a plurality of body marker member (65) operatively and moveably associated with the vertical alignment cord (60)(60') and each of their associated upper (61)(61'), intermediate (62)(62') and lower (63(63') alignment cords in each of the framework members (30)(31).

Furthermore, as can best be appreciated by reference to FIG. 5, each of the body marker member (65) comprises a generally cylindrical disk element (66) provided with laterally offset vertical (67) and horizontal (68) apertures that are dimensioned to slideably receive the vertical alignment cord (60) and one of the horizontal alignment cords (61)(62)(63) for reasons that will be explained shortly.

Figure 4:
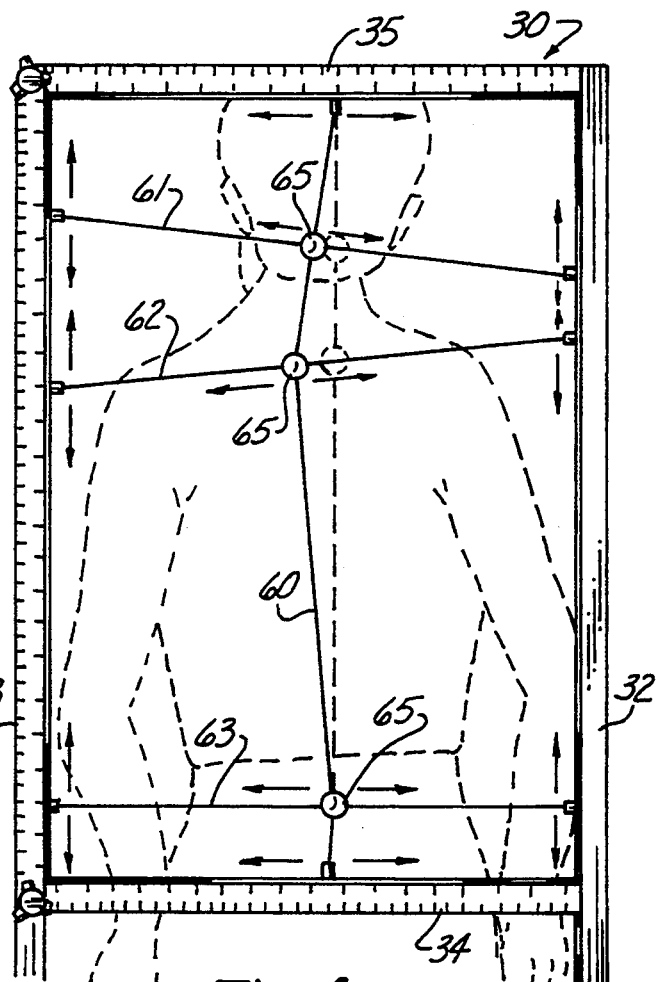
FIG. 4 is a partial front plan view of the posterior portion of the grid unit and associated registration units.
Figure 6:
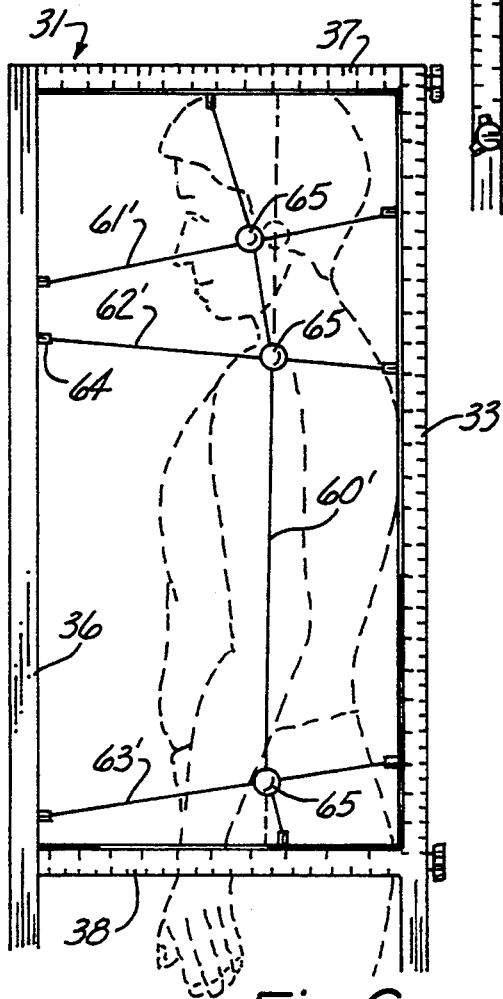
FIG. 6 is a partial front plan view of the lateral portion of the grid unit and associated registration units.

The operation of the apparatus 9100 can best be appreciated by reference to FIGS. 1, 4 and 6. As shown in FIG. 1, the patient (100) steps up onto the platform surface and is positioned in a relaxed upright stance with their right and left heels coming in contact with the leading edge of the extension arm (39'). At this juncture as shown in FIG. 2, the tendon guides (52)(53) are translated along the extension arm (39') so that the centerline indicia 954) are aligned with the midline of the patient's right and left calcaneus.

After the tendon guides (52)(53) have been aligned, the midline marker (50) is moved to a location half way between each of the tendon guides (52)(53) to provide the first vertical reference point which is then used to position the first vertical alignment cord (60) on the posterior framework member (30) by moving the cord anchor plates (64) on opposite ends of the vertical alignment cord (60) first into registration with the reading taken from the midline marker (50) and then into registration with the centerline of the patient's head.

Turning now to FIG. 4, it can be seen that once the vertical alignment cord (60) has been placed into its initial vertical registration (indicated by the dashed lines), the horizontal alignment cords (61)(62) and (63) are manipulated into registration with specific portions of the users anatomy to wit: the upper horizontal alignment cord (61) is aligned with the patient's mastoids; the intermediate horizontal alignment cord (62) is aligned with the acromioclavicular joints, and the lower horizontal alignment cord is aligned with the patient's iliac crest levels.

At this point, the posterior body markers (65) are positioned on the vertical alignment cord and the respective horizontal alignment cords in the following manner: the upper body marker (65) is positioned at the level of the patient's external occipital protuberance along the upper alignment cord (61); the intermediate body marker (65) is positioned along the intermediate alignment cord (62) at the level of the patient's spinous process of the second thoracic vertebra, and the lower body marker (65) is positioned along the lower alignment cord at the level of the patient's second sacral tuberch; thereby providing a visual and recordable record of the patient's posterior postural deficiencies.

Turning now to FIGS. 2 and 6, it can be seen that the lateral foot marker (51) is positioned along the lower cross-piece element (39) on the lateral framework member (31) at a point opposite the anterior aspect of the lateral malleolus of the patient. The second vertical alignment cord (60') has it lower end placed into registry with the lateral foot marker (51) and has its upper and placed into registry so that the upper end placed into registry so that the upper end of the second vertical registration cord (60') bisects the top of the patient's head at parietal eminence.

As can best be seen by reference to FIG. 6, once the lateral vertical alignment cord (60') has been placed into its initial vertical registration (indicated by the dashed lines), k the lateral horizontal alignment cords (61')(62') and (63') are manipulated into registration with other specific portions of the patient's anatomy to wit: the upper horizontal alignment cord (61') is aligned with the patient's bite line; the intermediate horizontal alignment cord (62') is aligned with the patient's acromioclavicular joints, and the lower horizontal alignment cord (63') is aligned with the patient's iliac crest.

At this point, the lateral body markers (65) are positioned on the second vertical alignment cord and the respective horizontal cords in the following manner: the upper lateral body marker (65) is positioned at the level of the patient's external auditory meatus; the intermediate lateral body marker (65) is set at the patient's acromioclavicular joint; and the lower lateral body marker (65) is positioned at the level of the patient's hip, thereby providing a visual and recordable record of the patient's lateral postural deficiencies.

When using the posterior framework member (30) as shown in FIG. 4, the following postural deviations can be determined: the difference between the left and right iliac crest; the left and right acromiodavicular joint, and the left and right mastoid. In addition, by using the lateral framework (31) shown in FIG. 6, the following postural deviations can be determined; the difference between the anterior and posterior iliac crest; the anterior and posterior acromodavicular joint; and the anterior and posterior bite line.

Having thereby described the subject matter of the present invention, it should be apparent that many substitutions, modifications and variations of the invention are possible in light of the above teachings. It is therefore to be understood that the invention as taught and described herein is only to be limited to the extent of the breadth and scope of the appended claims.

I claim:

1. An adjustable chiropractic diagnostic apparatus for determining a patient's lateral and posterior postural deficiencies wherein the apparatus comprises:
   a platform unit;
   a three-legged framework operatively associated with the platform unit and comprising a pair of generally rectangular and perpendicularly aligned framework members, including a posterior framework member and a lateral framework member; wherein, each of said framework members comprises a pair of vertical support legs provided with an upper cross-piece element and an intermediate cross-piece element; and
   a plurality of registration units, including a pair of vertical alignment cords, wherein each of the vertical alignment cords is moveably suspended between the upper and intermediate cross-piece elements of each framework member and a like plurality of horizontal alignment cords are moveably suspended between the vertical support legs of each framework member, whereby the vertical and horizontal alignment cords are moveable such that the intersection between the vertical and horizontal alignment cords may be registered with predetermined locations on a patient's anatomy to record the patient's postural deficiencies.

2. The apparatus as in claim 1, wherein, said like plurality of horizontal alignment cords comprise: an upper; and intermediate; and a lower horizontal alignment cord suspended within each of said framework members.

3. The apparatus as in claim 1, wherein, said plurality of registration units further comprises a plurality of body marker members, wherein, each of the plurality of body marker members are operatively and slideably connected on one of the vertical alignment cords and on one of the respective plurality of horizontal alignment cords.

4. The apparatus as in claim 1, wherein, the framework further comprises a lower cross-piece element operatively associated with one of the pair of framework members, and a perpendicularly aligned extension arm projecting outwardly from said lower cross-piece element.

5. The apparatus as in claim 4, wherein, the plurality of registration units further comprises a lateral foot marker, a pair of tendon guides, and a midline marker operatively associated with said lower cross-piece element and said extension arm.

6. The apparatus as in claim 5, wherein, said lower cross-piece element is disposed on said lateral framework member, the lateral foot marker is slideably disposed on said lower cross-piece element, and the pair of tendon guides and midline marker are slideably disposed with respect to said extension arm.

7. An adjustable chiropractic diagnostic apparatus for determining a patient's postural deficiencies, wherein, the apparatus comprises:
   a generally rectangular platform member having a raised platform surface;
   a framework operatively attached to said raised platform surface and comprising a generally rectangular posterior framework member, wherein, said posterior framework member comprises a pair of vertical support legs provided with an upper cross-piece element and an intermediate cross-piece element; and
   a plurality of registration units, including a vertical alignment cord moveably suspended between said upper and intermediate cross-piece elements and a plurality of horizontally alignment cords between said vertical support legs, whereby the vertical and horizontal alignment cords are moveable such that the intersections between the vertical and horizontal alignment cords may be registered with predetermined locations on a patient's anatomy to record the patient's postural deficiencies.

8. The apparatus as in claim 7, wherein, said plurality horizontal alignment cords comprise: an upper; an intermediate; and a lower horizontal alignment cord.

9. The apparatus as in claim 7, wherein, said plurality of registration units further comprises a plurality of body marker members, wherein, each body marker member is slideably disposed on said vertical alignment cord and a respective one of said plurality of horizontal alignment cords.

10. The apparatus as in claim 7, wherein, said raised platform surface is further provided with an extension arm disposed parallel to one side of the generally rectangular platform member, wherein, the extension arm is provided with a midline marker and a pair of raised tendon guides which are slideably disposed relative to said extension arm.

11. A method of measuring a patient's postural deficiencies using a framework mounted on a platform member, and including indicia bearing vertical support legs connected together by an upper indicia bearing cross-piece element and an intermediate indicia bearing cross-piece element connected together to form an elevated rectangular opening, wherein, the platform member is provided with an indicia bearing extension arm disposed proximate said framework, and including a slidable midline marker, and wherein, the framework is provided with a moveable vertical alignment cord suspended between the upper and intermediate indicia bearing cross-piece elements and a plurality moveable horizontal alignment cords which are suspended between the vertical support legs and operatively connected to the vertical alignment cord by a plurality of moveable body marker members comprising the steps of:
   a) placing a patient on the platform member and positioning the back of the patient's feet adjacent to the indicia bearing extension arm;
   b) positioning the midline marker on the extension arm at a point equidistant from the patient's feet;
   c) moving the lower end of the vertical alignment cord on the intermediate cross-piece element to a location corresponding to the position of the midline marker on the extension arm and moving the upper end of the vertical alignment cord on the upper cross-piece element to a position, wherein, the upper end of the vertical alignment cord bisects the patient's head;

d) aligning the plurality of horizontal alignment cords with different portions of the patient's anatomy;

e) moving the body marker members relative to specific locations on the patient's body;

f) recording the position of the body markers relative to the indicia bearing portions of the framework prior to chiropractic manipulation of the patient's body;

g) repeating steps a) thru e) after chiropractic manipulation of the patient's body;

h) recording the position of the body markers relative to the indicia bearing portions of the framework subsequent to chiropractic manipulation of the patient's body; and, i) making a comparison of the recorded values in steps f) and h) to analyze the effectiveness of the chiropractic manipulation on the patient's postural deficiencies.

* * * * *